(12) United States Patent
Krasikoff et al.

(10) Patent No.: US 8,808,262 B2
(45) Date of Patent: Aug. 19, 2014

(54) MEDICAL BRA ASSEMBLY FOR POST-SURGICAL BREAST RECONSTRUCTION AND COSMETIC BREAST PROCEDURES

(71) Applicant: ELN Group, LLC, Cary, IL (US)

(72) Inventors: Nina Krasikoff, Chicago, IL (US); Laurine Sargent, Chicago, IL (US); Eric Ladewig, Cary, IL (US)

(73) Assignee: ELN Group, LLC, Chicago, IL (US)

( * ) Notice: Subject to any disclaimer, the term of this patent is extended or adjusted under 35 U.S.C. 154(b) by 0 days.

(21) Appl. No.: 13/913,432

(22) Filed: Jun. 8, 2013

(65) Prior Publication Data

US 2013/0331808 A1    Dec. 12, 2013

Related U.S. Application Data

(60) Provisional application No. 61/657,496, filed on Jun. 8, 2012.

(51) Int. Cl.
| | | |
|---|---|---|
| *A61F 13/15* | (2006.01) | |
| *A61F 13/14* | (2006.01) | |
| *A61F 13/82* | (2006.01) | |
| *A61F 5/03* | (2006.01) | |

(52) U.S. Cl.
CPC ............. *A61F 13/14* (2013.01); *A61F 13/82* (2013.01); *A61F 13/141* (2013.01); *A61F 5/03* (2013.01); *A61F 13/145* (2013.01); *A61F 2013/15016* (2013.01)
USPC ................ 604/385.07; 604/385.09

(58) Field of Classification Search
CPC ......... A61F 5/03; A61F 13/14; A61F 13/141; A61F 13/143; A61F 13/145; A61F 13/146; A61F 13/148; A61F 2013/15016

USPC ......................... 604/385.07, 385.09
See application file for complete search history.

(56) References Cited

U.S. PATENT DOCUMENTS

| | | | | |
|---|---|---|---|---|
| 16,396 | A * | 1/1857 | Parker .......................... | 128/890 |
| 65,978 | A * | 6/1867 | Wilder ......................... | 128/890 |
| 3,840,012 | A * | 10/1974 | Rushton, Jr. .................. | 604/346 |
| 4,870,977 | A * | 10/1989 | Imonti ......................... | 128/890 |
| 5,743,272 | A * | 4/1998 | Kocher, Jr. .................... | 128/846 |
| 5,782,672 | A * | 7/1998 | Woodley ........................ | 450/57 |
| 7,921,851 | B2 * | 4/2011 | Kurz et al. .................... | 128/889 |
| 7,938,122 | B2 | 5/2011 | Clark | |
| 2002/0029010 | A1 * | 3/2002 | Augustine et al. .............. | 602/41 |
| 2006/0116632 | A1 * | 6/2006 | Gillan ........................... | 604/74 |
| 2009/0283101 | A1 * | 11/2009 | Mans ............................ | 128/890 |

* cited by examiner

*Primary Examiner* — Lynne Anderson
(74) *Attorney, Agent, or Firm* — Drinker Biddle & Reath LLP

(57) ABSTRACT

A medical bra assembly facilitates post-surgical care for a patient having undergone a breast reconstruction or cosmetic surgical procedure. The medical bra has a cup with an inside surface. The assembly includes (a) an absorptive skirt bandage attachable to a lower portion of the bra cup inside surface for absorbing secreted bodily fluids from a post-surgical patient's surgical incision, (b) a nipple tube bandage for encasing and absorbing secreted bodily fluids from the patient's reconstructed nipple, (c) a half-moon dome bandage interposable between the nipple tube bandage and the bra cup inside surface, which covers and protects the nipple tube bandage adhered to the patient's breast skin, and (d) an areola pad bandage interposable between the patient's breast skin and the bra cup inside surface for absorbing secretions from a re-pigmented tattoo region around the patient's reconstructed nipple when the bra is being worn by the patient.

19 Claims, 3 Drawing Sheets

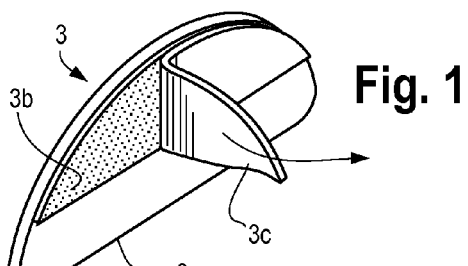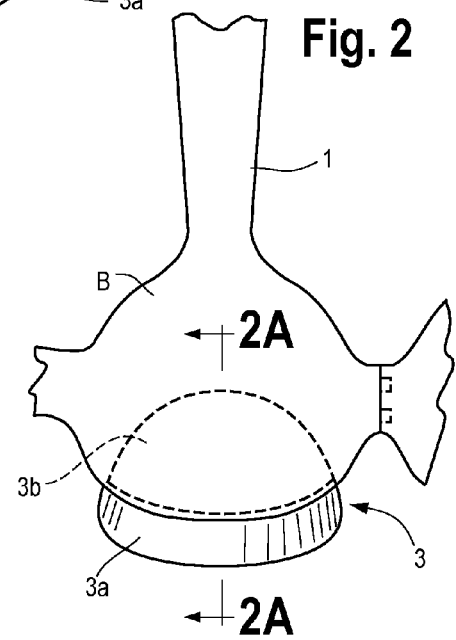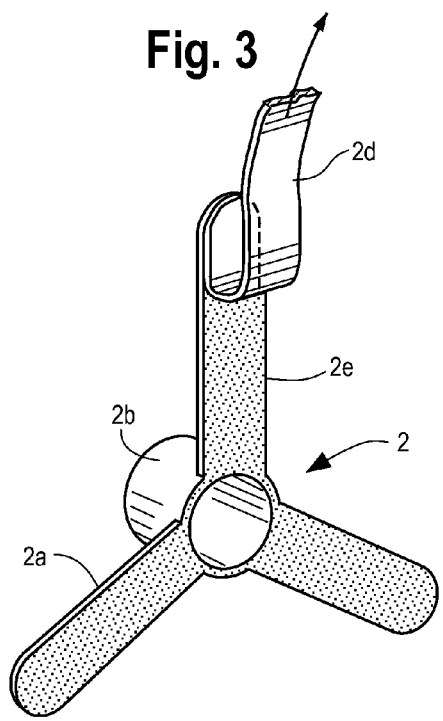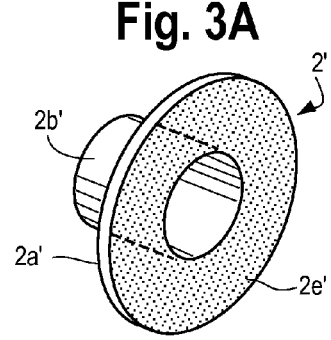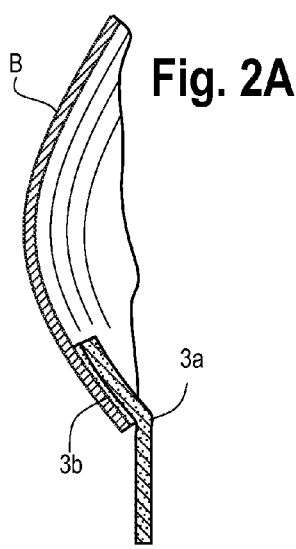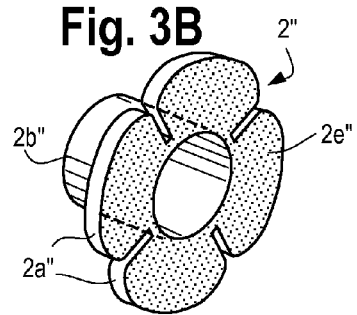

MEDICAL BRA ASSEMBLY FOR POST-SURGICAL BREAST RECONSTRUCTION AND COSMETIC BREAST PROCEDURES

CROSS-REFERENCE TO RELATED APPLICATION

This application is related to and claims priority benefits U.S. Provisional Patent Application Ser. No. 61/657,496 filed on Jun. 8, 2012, entitled "Medical Bra Assembly For Post-Surgical Fluid Management". The '496 provisional application is hereby incorporated by reference herein in its entirety.

BACKGROUND

The present invention relates to medical devices and, more particularly, to a medical bra assembly or kit with accessories including bandages designed to aid and support a patient's post-surgical healing process following breast reconstruction and other types of breast surgical procedures.

SUMMARY

The present medical bra assembly or kit includes garments and accessories to accommodate a patient's specific and personal needs following a mastectomy, cosmetic surgery, breast reduction, breast enhancements, nipple reconstruction and other breast surgical procedures. Because of the many difficulties and frustrations that accompany post-surgical care and procedures, the present integrated system incorporates a medical bra and accessories to provide support, protection, comfort and hygiene, all which are directed to enhancing the patient's wellbeing and recovery following breast surgery.

The medical bra is preferably made of breathable, ultra-soft materials to accommodate sensitive skin, particularly after the patient has undergone radiation treatment or chemotherapy. The medical bra assembly includes:
(a) an absorptive skirt bandage;
(b) a nipple tube bandage;
(c) a half-moon dome bandage for covering and protecting the nipple tube bandage;
(d) an areola pad bandage for managing bleeding in the area surrounding nipples after areola re-pigmentation and cosmetic tattooing procedure.

The accessories are discretely designed to accommodate specific needs during the post-surgical healing process. Comfort, protection, hygiene and dignity are important to the patient's overall post-surgical healing process.

In the integrated support system, the nipple tube bandage is shaped as a cylinder, in one embodiment having a diameter of ½" and graduating incrementally in size by ¼", to adjust to the patient's nipple size and physique. The cylinder is preferably made of a soft and supportive biodegradable material, lined with absorbent and gentle non-stick film to protect the nipples during the healing process. The bottom of the nipple tube bandage is connected by a plurality, preferably 3 or 4, easy peel-off, bandage style strips and can be easily attached to the breast by the adhesive sides of the strips. The strips are preferably made from materials similar to surgical tape to provide support and stability to the nipple tube bandage without causing irritation to delicate skin following surgery.

The replaceable and disposable nipple tube bandage promotes hygiene by allowing patients to exchange them as often as needed to prevent infection and to provide gentle support to the sensitive reconstructed nipples during the healing process. The nipple tube bandage will also keep the bra fresh and clean.

The medical bra preferably has a front snap closure to accommodate limited mobility of the patient following surgery and can be fastened and unfastened with ease. The bra straps are preferably slightly wider than a normal bra strap, adjustable and padded to provide extra security and a more comfortable fit.

The medical bra is preferably formed with thin and firm foam cups covered with an attractive material such as satin, lace, and other cheerfully printed fabrics. The cups are preferably lined with superfine, soft and hygienic cotton. Each foam cup conceals the supportive nipple tube bandage. The cups are preferably seamless to provide comfort and protection for sensitive skin. The cups are preferably molded for firmer support. The stabilizing molded cups of low elasticity microfiber and wider straps provide direct support and minimize movements of the breasts during activity.

In the integrated support system, the half-moon dome bandage can be worn with most any bra in order to conceal the nipple tube bandage. This option provides the patient more flexibility in choosing the style of bra that most comfortable to the wearer. The half-moon dome bandage preferably has a peel-off adhesive material on the back, which enables patients to position the dome bandage securely inside the bra cup for a better fit.

The back of the bra is preferably made of comfortable elastic Lycra and microfiber which provides elasticity and a smooth fit.

Suggested materials for the medical bra include breathable, superfine and soft cotton, microfiber, Lycra, Spandex, floral-print satin and lace. The foam cups are preferably formed from acetate or similar material with decorative lace and super microfiber bonded together without seams for comfort. The foregoing materials are suitable for sensitive skin, especially after radiation or chemotherapy.

High-functioning materials are preferably made of coordinated superfine microfiber fabrics and ultra soft cotton, which is washable, breathable and quick-drying.

The final cosmetic procedure in the breast reconstruction process is the areola re-pigmentation and tattooing. Slight bleeding is typical during and following this procedure. To protect the bra from blood as a result of this procedure, a nonstick, preferably circularly shaped areola pad bandage, which is made from an ultra-thin, absorptive and flexible cushion that is comfortable to wear and keeps the bra clean and fresh. The areola pad bandage can be securely attached to and positioned inside the bra cup by an adhesive backing covered with a peel-off protective strip or layer.

Following reconstructive surgery, sutures and incisions continue to bleed, weep or otherwise secrete bodily fluids, which makes it necessary to absorb these secretions. An attachable absorptive skirt bandage accomplishes this function. The absorptive skirt bandage is preferably made out of a flexible panel. The upper part of the absorptive skirt bandage has an adhesive strip and can be attached to the lower edge of the bra cup inside surface, while the bottom part of the absorptive skirt bandage extends below the lower edge of the bra and has a thin, panty liner-type pad which absorbs blood and bodily fluids secreting from the sutures and incisions from surgery. The absorptive skirt bandage promotes hygiene and keeps the bra fresh and clean. This thin absorptive skirt bandage absorbs secretions and can be recyclable, biodegradable and disposable.

The medical bra assembly's absorptive skirt bandage, nipple tube bandage, half-moon dome bandage and areola pad bandage provide convenience, comfort and hygiene and help to prevent infection and combat swelling around sutures and reconstructed breast tissue. Patients should be strongly encouraged to carry with them an extra set of accessories in order to exchange them as often as necessary. The medical bra package thus includes accessories to offer the patients options to suit their personal needs as well as being functional and practical.

A medical bra assembly facilitates post-surgical care for a patient having undergone a breast reconstruction or cosmetic surgical procedure. The medical bra comprises a cup having an inside surface. The assembly comprises:

(a) an absorptive skirt bandage having an upper portion and a lower portion, the absorptive skirt bandage upper portion having an adhesive surface attachable to a lower portion of the bra cup inside surface, the absorptive skirt bandage bottom portion extending below a lower edge of the bra cup and having an absorptive portion for absorbing secreted bodily fluids from a post-surgical patient's surgical incision;

(b) a nipple tube bandage for encasing the patient's reconstructed nipple, the nipple tube bandage comprising an absorbent nipple tube for absorbing secreted bodily fluids from the post-surgical patient's reconstructed nipple and an adhesive portion for adhering the nipple tube bandage to the patient's breast skin;

(c) a half-moon dome bandage having an absorptive surface and an oppositely-facing adhesive surface, the half-moon dome bandage interposable between the nipple tube bandage and the bra cup inside surface, the half-moon dome bandage covering and protecting the nipple tube bandage adhered to the patient's breast skin;

(d) an areola pad bandage having an absorptive surface and an oppositely-facing adhesive surface, the areola pad bandage interposable between the patient's breast skin and the bra cup inside surface, the areola pad bandage capable of absorbing bleeding from a re-pigmented tattoo region around the patient's reconstructed nipple when the bra is being worn by the patient.

In a preferred embodiment of the medical bra assembly, the absorptive skirt bandage comprises an absorptive layer, a peel-off layer and an adhesive layer interposed between the absorptive layer upper portion and the peel-off layer. The adhesive layer is exposable for adhering the absorptive skirt bandage to the bra cup inside surface when the peel-off layer is removed.

In a preferred embodiment of the medical bra assembly, the nipple tube bandage adhesive portion comprises at least one adhesive strip extending laterally away from the nipple tube. The at least one adhesive strip comprises an adhesive surface facing away from the nipple tube and a peel-off layer, the adhesive surface exposable for adhering the nipple tube bandage to the patient's breast skin when the peel-off layer is removed. The at least one adhesive strip can comprise a plurality of propeller-style adhesive strips, a plurality of cloverleaf-style adhesive strips, or a hat brim-style adhesive portion extending laterally from the nipple tube.

In a preferred embodiment of the medical bra assembly, the half-moon dome bandage comprises an absorptive layer, a peel-off layer and an adhesive layer interposed therebetween. The adhesive layer is exposable for adhering the half-moon dome bandage to the bra cup inside surface when the peel-off layer is removed.

In a preferred embodiment of the medical bra assembly, the areola pad bandage comprises an absorptive layer, a peel-off layer and an adhesive layer interposed between the absorptive layer and the peel-off layer. The adhesive layer is exposable for adhering the areola pad bandage to the bra cup inside surface when the peel-off layer is removed.

A method provides post-surgical care for a patient having undergone a breast reconstruction or cosmetic surgical procedure. At least a portion of the post-surgical care is provided during the wearing of a medical bra comprising a cup having an inside surface. The method comprises:

(a) adhering an absorptive skirt bandage to a lower portion of the bra cup inside surface, the adhesive skirt bandage having an upper portion and a lower portion, the absorptive skirt bandage upper portion having an adhesive surface and a bottom portion extending below a lower edge of the bra cup and having an absorptive portion for absorbing secreted bodily fluids from the post-surgical patient's surgical incision;

(b) encasing the patient's reconstructed nipple in a nipple tube bandage comprising an absorbent nipple tube for absorbing secreted bodily fluids from the post-surgical patient's reconstructed nipple and an adhesive portion for adhering the nipple tube bandage to the patient's breast skin;

(c) adhering a half-moon dome bandage to the bra cup inside surface, the half-moon dome bandage having an absorptive surface and an oppositely-facing adhesive surface, the half-moon dome bandage interposable between the nipple tube bandage and the bra cup inside surface, the half-moon dome bandage covering and protecting the nipple tube bandage adhered to the patient's breast skin;

(d) adhering an areola pad bandage to the bra cup inside surface, the areola pad bandage having an absorptive surface and an oppositely-facing adhesive surface, the areola pad bandage interposable between the patient's breast skin and the bra cup inside surface, the areola pad bandage capable of absorbing bleeding from a re-pigmented tattoo region around the patient's reconstructed nipple when the bra is being worn by the patient.

In a preferred method embodiment, the absorptive skirt bandage comprises an absorptive layer, a peel-off layer and an adhesive layer interposed between the absorptive layer upper portion and the peel-off layer. The adhesive layer is exposable for adhering the absorptive skirt bandage to the bra cup inside surface when the peel-off layer is removed.

In a preferred method embodiment, the nipple tube bandage adhesive portion comprises at least one adhesive strip extending laterally away from the nipple tube. The at least one adhesive strip comprises an adhesive surface facing away from the nipple tube and a peel-off layer. The adhesive surface is exposable for adhering the nipple tube bandage to the patient's breast skin when the peel-off layer is removed. The at least one adhesive strip can comprise a plurality of propeller-style adhesive strips, a plurality of cloverleaf-style adhesive strips, or a hat brim-style adhesive portion extending laterally from the nipple tube.

In a preferred method embodiment, the half-moon dome bandage comprises an absorptive layer, a peel-off layer and an adhesive layer interposed therebetween. The adhesive layer is exposable for adhering the half-moon dome bandage to the bra cup inside surface when the peel-off layer is removed.

In a preferred method embodiment, the areola pad bandage comprises an absorptive layer, a peel-off layer and an adhesive layer interposed between the absorptive layer and the peel-off layer. The adhesive layer exposable for adhering the areola pad bandage to the bra cup inside surface when the peel-off layer is removed.

BRIEF DESCRIPTION OF THE DRAWING(S)

FIG. 1 is a perspective view of an absorptive skirt bandage showing the absorptive layer, the adhesive layer and the peel-off layer.

FIG. 2 is a front view of a medical bra cup with the absorptive skirt bandage adhered to the lower inside surface of the cup and in which the absorptive layer extends below the lower edge of the bra cup.

FIG. 2A is a side cross-sectional view, taken in the direction of arrows 2A-2A in FIG. 2, of the absorptive skirt bandage adhered to the lower inside surface of the medical bra cup.

FIG. 3 is a perspective view of a nipple tube bandage showing the nipple tube, the propeller-style adhesive strips and the peel-off layer.

FIG. 3A is a perspective view of a first alternative embodiment of a nipple tube bandage with a hat brim-style adhesive portion.

FIG. 3B is a perspective view of a second alternative embodiment of a nipple tube bandage with a cloverleaf-style adhesive portion

DETAILED DESCRIPTION OF PREFERRED EMBODIMENT(S)

Figure 4:
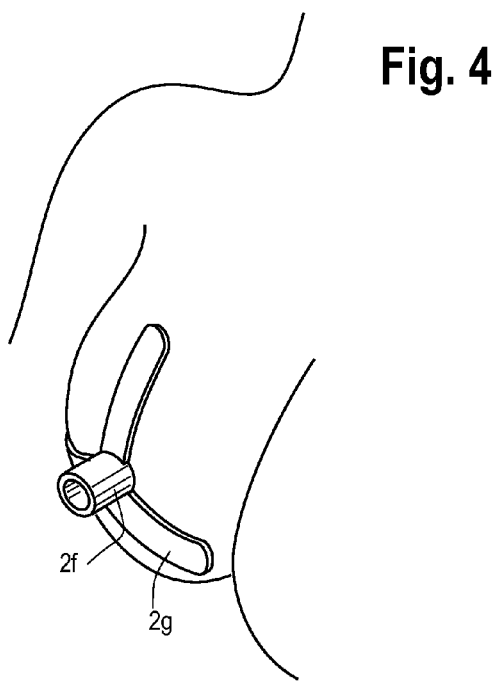
FIG. 4 is a perspective view of the nipple tube bandage adhered to the skin of a patient's breast.

Referring first to FIG. 1, an absorptive skirt bandage 3 includes an absorptive layer 3a, an adhesive layer 3b and a peel-off layer 3c. In FIG. 2, a medical bra cup B with the absorptive skirt bandage 3 is adhered to the lower inside surface of cup B. FIG. 2 also shows medical bra strap 1, which is slightly wider than a normal non-medical bra strap. The medical bra is also shown in FIG. 2 as having a front snap closure to accommodate limited mobility of the patient following surgery and can be fastened and unfastened with ease.

In FIG. 2A, absorptive skirt bandage 3 is shown in a side cross-sectional view taken in the direction of arrows 2A-2A in FIG. 2. As shown, adsorptive skirt bandage 3 has its peel-off layer removed to expose adhesive layer 3b, which is adhered to the lower inside surface of medical bra cup B such that adsorptive layer 3a extends downwardly from the lower edge of bra cup B. In most breast surgery and reconstruction procedures, the first post-surgery stage involves a stitched wound at the site of the incision of the patient's breast that corresponds to the lower edge of an adjacent medical bra cup. Adsorptive layer 3a collects fluid secretions from the patient's wound that might otherwise stain the medical bra cup or clothing located in the area surrounding the medical bra cup.

The second stage of most breast surgery and reconstruction procedures involves reconstruction of the patient's nipple. FIG. 3 shows a nipple tube bandage 2 for the post-surgery stage of nipple reconstruction. Nipple tube bandage 2 includes a nipple tube 2b, normally formed from an absorbent material, and a plurality of adhesive strips, one of which is designated in FIG. 3 as propeller-style adhesive strip 2a. Peel-off layer 2d is shown as being partially removed to expose adhesive surface 2e, which gently adheres to the patient's breast skin to position nipple tube 2b around the reconstructed nipple. In another embodiment, nipple tube 2b may be found formed from a firm foam material, about 0.5 inch in diameter, and lined inside with absorptive, soft and breathable cotton or microfiber for comfort and hygiene.

FIG. 3A shows a first alternative embodiment of nipple tube bandage 2', in which the propeller-style strips in FIG. 3 are replaced with a hat brim-style adhesive portion 2a'. A peel-off layer (not shown) is removed to expose adhesive surface 2e', which gently adheres to the patient's breast skin to position nipple tube 2b' around the reconstructed nipple.

FIG. 3B shows a second alternative embodiment of nipple tube bandage 2", in which the propeller-style strips in FIG. 3 are replaced with a plurality of cloverleaf-style adhesive portions, one of which is designated in FIG. 3B as cloverleaf-style adhesive portions 2a". A peel-off layer (not shown) is removed to expose adhesive surface 2e", which gently adheres to the patient's breast skin to position nipple tube 2b" around the reconstructed nipple.

FIG. 4 shows the positioning of the nipple tube bandage to the skin of a patient's breast in the nipple area. As shown, nipple tube 2f is positioned to surround the patient's reconstructed nipple. The propeller-style adhesive strips, one of which is designated in FIG. 4 as adhesive strip 2g, gently adhere to the patient's skin to secure nipple tube 2f around the reconstructed nipple. The patient's nipple is nested in nipple tube 2f for protection and support of the sensitive skin of the reconstructed nipple.

Figure 5A:
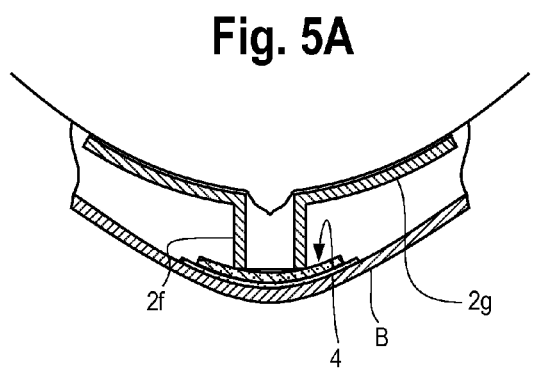
FIG. 5A is a top cross-sectional, view taken in the direction 5A-5A in FIG. 5, showing a nipple tube bandage adhered to a patient's breast and residing within the medical bra cup, and which has a half-moon dome bandage adhered to the inside surface of the medical bra cup and interposed between the half-moon dome bandage and nipple tube bandage.
Figure 5:
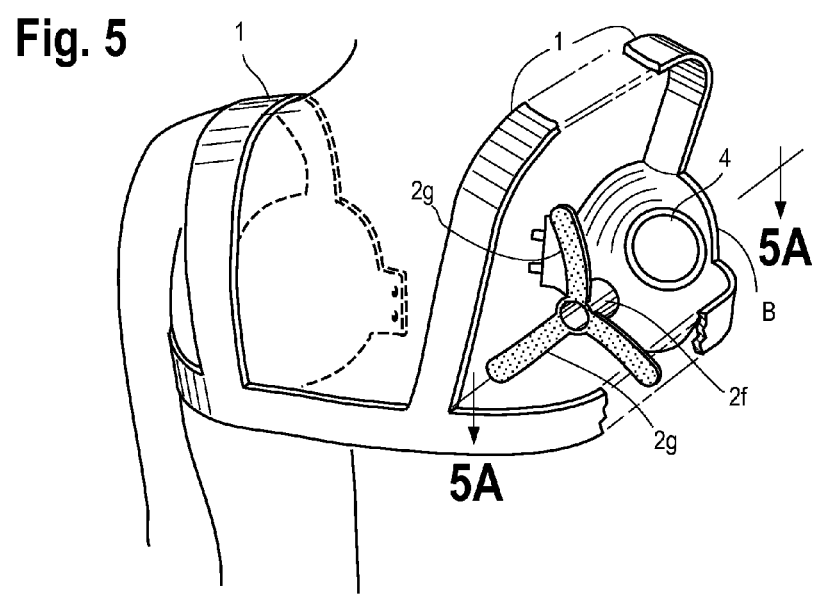
FIG. 5 is an exploded back perspective view of the medical bra with a half-moon dome bandage adhered to the inside surface of a medical bra cup, with the nipple tube bandage positioned to be adhered to a patient's breast and then residing within the medical bra cup.

FIG. 5 shows a view of a medical bra from the back, with bra straps 1 preferably formed slightly wider than a normal bra strap. Straps 1 are adjustable and padded to provide a comfortable fit on the patient. The medical bra shown in FIG. 5 has its front closure unsnapped. A half-moon dome bandage 4 is adhered to the inside surface of medical bra cup B, with the nipple tube bandage positioned to be adhered by propeller-style adhesive strips 2g to a patient's breast skin such that nipple tube 2f is positioned around the patient's reconstructed nipple. Once adhered to the patient's breast, the nipple tube bandage then resides within medical bra cup B.

In FIG. 5A, the nipple tube bandage of FIG. 5 is shown in a top cross-sectional view taken in the direction 5A-5A. The nipple tube bandage is adhered to the patient's breast skin by adhesive strips 2g such that nipple tube 2f is positioned around the patient's reconstructed nipple and resides within the medical bra cup B. A half-moon dome bandage 4 (shown more fully in FIG. 6) is adhered to the inside surface of medical bra cup B and is interposed between half-moon dome bandage 4 and nipple tube 2f.

Figure 6:
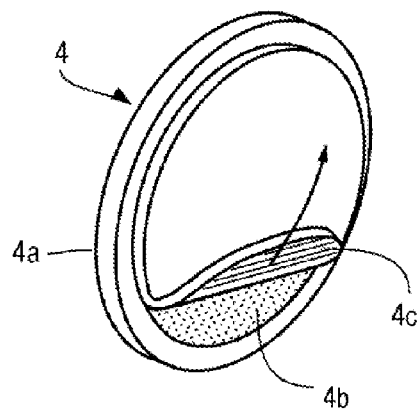
FIG. 6 is a perspective view of a half-moon dome bandage showing the absorptive layer, the adhesive layer and the peel-off layer.

In FIG. 6, half-moon dome bandage 4 is shown as including an absorptive layer 4a, an adhesive layer 4b and a peel-off layer 4c. Half-moon dome bandage 4 is designed to conceal the nipple tube bandage when the medical bra is being worn, thereby providing the patient more flexibility in choosing the style of bra they are most comfortable wearing. Half-moon dome bandage 4 is preferably made from thin, lightweight, firm and flexible materials for a comfortable and smooth fit inside the bra and to simultaneously protect the patient's nipple from external or other applied pressure.

Figure 7:
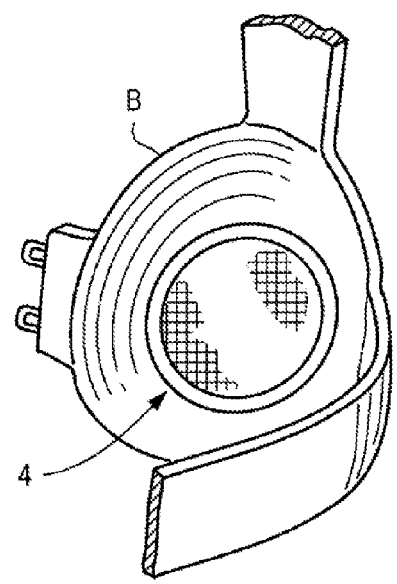
FIG. 7 is a back perspective view of a medical bra cup with the half-moon dome bandage adhered to the inside surface of the medical bra cup.
Figure 8:
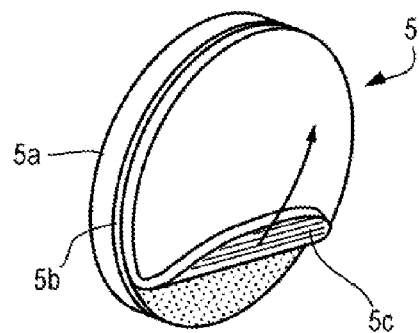
FIG. 8 is a perspective view of an areola pad bandage showing the absorptive layer, the adhesive layer and the peel-off layer.

FIGS. 7 and 8 pertain to post-surgery care following the third stage of most breast surgery and reconstruction procedures, which involves tattooing of a ring of color or pigmentation around the reconstructed nipple to replicate the areola. FIG. 8 shows areola pad bandage 5, which includes an absorptive layer 5a, adhesive layer 5b and peel-off layer 5c. As shown in FIG. 7, when adhered on the inside medical bra cup B, areola pad bandage 4 protects bra cup B from blood and other fluid typically secreted after a tattooing procedure. Areola pad bandage 4 promotes hygiene and is preferably made from the ultra-thin, absorptive and flexible cushion, which is comfortable to wear and keeps the bra cup clean and fresh While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What is claimed is:

1. A nipple tube bandage comprising:
    a tube sized to encase a patient's nipple and comprises a foam material, wherein the tube has two open ends; and
    an adhesive portion attached to one end of the tube and the adhesive portion is adapted to adhere the nipple tube bandage to a patient's skin.
2. The nipple tube bandage of claim 1, wherein the tube further comprises an absorbent material which is adapted to absorb secreted bodily fluids.
3. The nipple tube bandage of claim 1, wherein the tube has a cylinder shape.
4. The nipple tube bandage of claim 1, wherein the tube has a diameter of about 0.5 inch.
5. The nipple tube bandage of claim 1, wherein the adhesive portion comprises at least one adhesive strip extending laterally away from the tube, the at least one adhesive strip comprising an adhesive surface facing away from the tube.
6. The nipple tube bandage of claim 5, wherein the at least one adhesive strip further comprises a peel-off layer, and the adhesive surface is exposed to adhere to the patient's skin when the peel-off layer is removed.
7. The nipple tube bandage of claim 1, wherein the adhesive portion comprises at least one adhesive pad extending radially away from the tube, the at least one adhesive strip comprising an adhesive surface facing away from the tube.
8. The nipple tube bandage of claim 7, wherein the at least one adhesive strip further comprises a peel-off layer, and the adhesive surface is exposed to adhere to the patient's skin when the peel-off layer is removed.
9. The nipple tube bandage of claim 1, wherein the adhesive portion comprises an annular adhesive strip extending radially away from the tube, the annular adhesive strip comprising an adhesive surface facing away from the tube.
10. The nipple tube bandage of claim 9, wherein the annular adhesive strip further comprises a peel-off layer, and the adhesive surface is exposed to adhere to the patient's skin when the peel-off layer is removed.
11. A nipple tube bandage comprising:
    a tube sized to encase a patient's reconstructed nipple and the tube is formed from an absorbent material which is adapted to absorb secreted bodily fluids; and
    a plurality of adhesive portions attached to the tube and which is adapted to adhere the nipple tube bandage to a patient's skin.
12. The nipple tube bandage of claim 11, wherein the tube has a cylinder shape.
13. The nipple tube bandage of claim 11, wherein the tube has a diameter of about 0.5 inch.
14. The nipple tube bandage of claim 11, wherein each of the plurality of adhesive portions comprises an adhesive surface facing away from the tube.
15. The nipple tube bandage of claim 14, wherein each of the plurality of adhesive portions further comprises a peel-off layer, and the adhesive surface is exposed to adhere to the patient's skin when the peel-off layer is removed.
16. The nipple tube bandage of claim 11, wherein the plurality of adhesive portions comprises four adhesive portions.
17. A method comprising:
    encasing a patient's nipple in a nipple tube bandage comprising a foam tube and an adhesive portion, wherein the foam tube has two open ends and the adhesive portion is attached to one end of the foam tube;
    removing a peel-off layer from an adhesive surface of the adhesive portion; and
    adhering the adhesive surface to the patient's skin.
18. The method of claim 17, wherein the adhesive portion comprises at least one adhesive strip extending laterally away from the tube.
19. The method of claim 17, wherein the adhesive portion comprises at least one adhesive pad extending radially away from the tube.

* * * * *